United States Patent [19]

Dignam, deceased, et al.

[11] Patent Number: 4,692,142
[45] Date of Patent: Sep. 8, 1987

[54] SUTURELESS INFUSION CANNULA FOR OPHTHALMIC SURGERY

[76] Inventors: Bernard J. Dignam, deceased,, late of Belvedere; Bonnie M. Dignam, heiress, 250 Bay View Ave., Belvedere, both of Calif. 94920

[21] Appl. No.: 832,906

[22] Filed: Feb. 24, 1986

[51] Int. Cl.$^4$ .............................................. A61M 5/00
[52] U.S. Cl. .................................... 604/51; 604/117; 604/272
[58] Field of Search ..................... 604/280, 117, 8, 93, 604/174, 175, 178, 180, 264, 272, 294, 51

[56] References Cited

U.S. PATENT DOCUMENTS

| | | | |
|---|---|---|---|
| 3,726,284 | 4/1973 | Parker | 604/8 |
| 3,776,239 | 12/1973 | Cooley | 604/117 |
| 4,380,234 | 4/1983 | Kamen | 604/180 |
| 4,400,169 | 8/1983 | Stephen | 604/280 X |

Primary Examiner—Stephen C. Pellegrino
Attorney, Agent, or Firm—Townsend and Townsend

[57] ABSTRACT

An ocular infusion cannula containing a shoulder and a flange may be retained in the sclera during ophthalmic surgery without the use of sutures or vacuum techniques. The shoulder is sufficiently narrow to permit the sclera to expand and contract as it passes over due to resiliency of the sclera, and the gap between the shoulder and the flange is of appropriate width to retain the sclera while permitting a minimum axial slippage.

6 Claims, 4 Drawing Figures

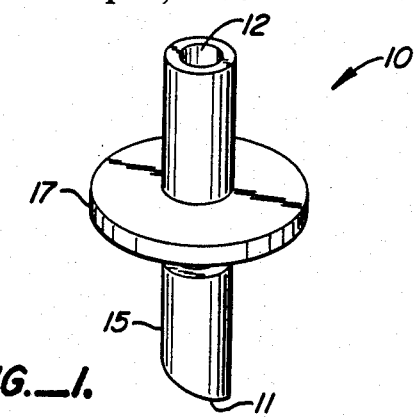
FIG.—1.
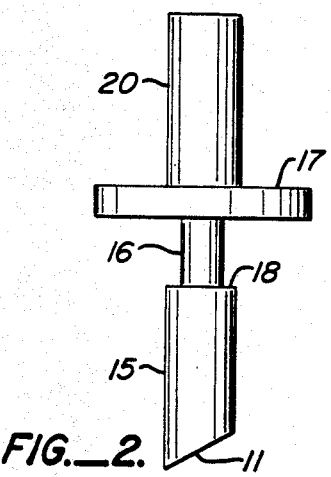
FIG.—2.
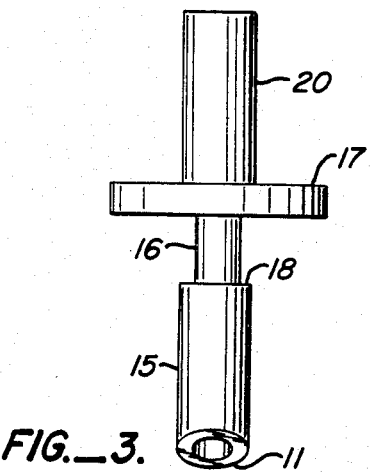
FIG.—3.
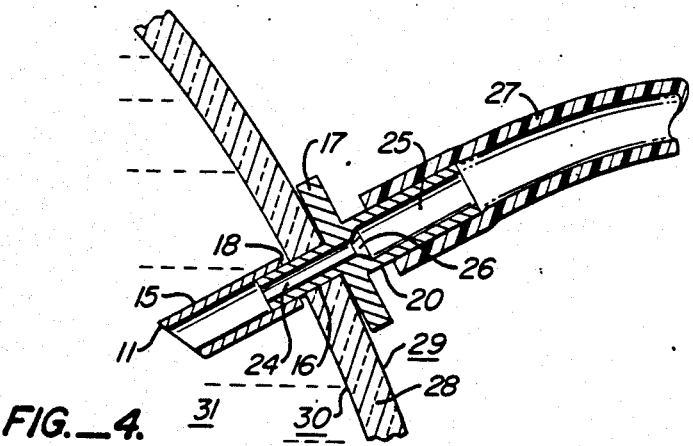
FIG.—4.

SUTURELESS INFUSION CANNULA FOR OPHTHALMIC SURGERY

BACKGROUND OF THE INVENTION

This invention relates to cannulas, and particularly to cannulas intended for insertion into the ocular cavity for purposes of regulating or maintaining humoral pressure during opthalmic surgery.

Surgical procedures involving the eyeball, particularly retinal procedures, require the introduction of one or more instruments into the eye. This results in the leakage of fluid from the interior of the eye, and in many procedures fluid is intentionally drained. Infusion cannulas are therefore used in conjunction with these instruments to maintain or regulate the fluid pressure inside the eye. While infusion lines contiguous with the other surgical instruments have been used, the use of independent infusion sites are preferred in surgical procedures in view of certain advantages which they offer.

Methods for holding the cannula in place after insertion have included vacuum attachment features and suturing. Structures utilizing vacuum require vacuum sources and close regulation of the degree of vacuum. Suturing, on the other hand, is a time-consuming procedure and aggravates the trauma in the sclera at the point of entry of the cannula.

SUMMARY OF THE INVENTION

A novel cannula has now been developed which overcomes the disadvantages of cannulas of the prior art. The cannula of the present invention contains a neck portion of narrower diameter than the remainder of the cannula, the neck portion terminating at its outer end in a flange. The shoulder at the base of the neck portion holds the cannula in place after insertion into the eyeball past the sclera. The flange serves as a stop to limit the depth of insertion. The sclera thus stably rests between the shoulder and the flange, the resilience of the sclera being sufficient to prevent inadvertent slippage back over the forward, wider end of the cannula. The result is an infusion cannula which is self-retaining without sutures and yet can be easily removed with a moderate degree of exertion.

BRIEF DESCRIPTION OF THE DRAWINGS

FIG. 1 is a perspective view of a cannula in accordance with the present invention.

FIG. 2 is a side elevation of the cannula of FIG. 1.

FIG. 3 is a second side elevation of the cannula of FIG. 1, rotated 90° from the view shown in FIG. 2.

FIG. 4 is a cutaway view of the cannula of FIG. 1 inserted in an eyeball and attached to external fluid delivery tubing.

DETAILED DESCRIPTION OF THE INVENTION AND PREFERRED EMBODIMENTS

The figures show one embodiment of the present invention, selected as illustrative of the features of the invention. FIG. 1 shows a cannula 10, which is essentially a hollow tube open at both ends. The piercing end 11, which is the forward end of the cannula, is the end which enters the ocular cavity, whereas the supply end 12 or rearward end is connected to a fluid or fluid pressure source, generally by external tubing. In the embodiment shown, the supply end 12 is sized to be snugly inserted inside flexible fluid delivery tubing in a fluid-tight manner. Other means of securement to a fluid delivery tube may be substituted, such as clamping devices or threaded connections. Any conventional manner capable of withholding fluid under pressure may be used.

In the side elevation views shown in FIGS. 2 and 3, it may be seen that the cannula contains a first tube segment 15 or forward portion, a second tube segment 16 or neck portion, and a flange 17. The neck portion 16 is of lesser diameter than the forward portion 15, the two portions forming a shoulder 18 at the point of transition. In preferred embodiments, such as that shown, the forward and neck portions are coaxial, and the shoulder is a flat circumferential surface perpendicular to the axis of the cannula, encircling the cannula at substantially constant width. The width may vary, but will generally be selected such that it is sufficient to retain the sclera as the hole in the sclera contracts around the neck portion 16 due to the resiliency of the sclera once it has passed over the shoulder 18. In most applications, a width ranging from about 0.01 mm to about 0.30 mm, preferably from about 0.02 mm to about 0.10 mm, will provide the best results. The difference in diameter between the neck and forward portions of the cannula is conveniently achieved by fusing together two hypodermic needles of appropriate diameter. As an example, the diameter of the neck portion may be 20-gauge with a 19-gauge forward portion.

The flange 17 is spaced at a distance apart from the shoulder 18 sufficient to retain the thickness of the sclera, and thus preferably slightly larger than a typical sclera thickness. This may vary, although in general a distance ranging from about 0.5 mm to about 5.0 mm, preferably from about 1.0 mm to about 2.0 mm, will provide the best results. The width of the flange 17 itself may be considerably greater than the width of the shoulder 18, since the flange will be retained outside the eyeball as a stop limiting the degree of insertion of the cannula. The width of the flange is thus even less critical, and in most applications will be at least about 0.5 mm, preferably at least about 1.0 mm.

The piercing end 11 of the cannula is cut at an acute angle with respect to the cannula axis to facilitate piercing of the sclera.

The cannula in the embodiment shown has a third tube segment 20 extending backward from the rear of the flange 17. This tube segment is of larger diameter than the neck portion 16, and is preferably of an external diameter suitable for the attachment of a pressurized fluid delivery line, as mentioned above.

The cutaway view in FIG. 4 shows the interior of the cannula, as well as its method of securement to a sclera and to fluid delivery tubing. The central bore 24 of the cannula is of lesser diameter than the bore 25 of the outer tube segment 20, due to the differences in diameter of these segments themselves. To promote smooth fluid flow in the transition between these bores of different diameter, the bore 25 of the outer tube segment contains a tapering portion 26 to connect the bores. This view also shows a fluid delivery line in the form of flexible tubing 27 which is snug-fit over the exterior of the outer tube segment 20, leading to a pressurized fluid supply (not shown). Also visible in this drawing is the sclera 28, and the fact that the gap between the shoulder 18 and the flange 17 is slightly greater than the thickness of the sclera 28.

To install the cannula for surgical purposes, one pierces the external surface 29 of the sclera 28 with the piercing end 11 of the cannula, and advances the cannula forward into the interior of the eyeball until the shoulder 18 passes the internal surface 30 of the sclera. The sclera then rests between the shoulder 18 and the flange 17 and closes around the neck portion 16 due to its own resiliency. The fluid delivery line 27 is attached prior to insertion of the cannula, and once insertion is completed, fluid pressure is applied through the fluid delivery line to communicate with the interior 31 of the eyeball. The surgical operation then proceeds, generally involving instruments piercing the eyeball at other points. Once the operation is completed, the cannula is removed by pulling outward while applying gentle pressure on the scleral surface 29 immediately adjacent to the cannula, using common forceps.

The foregoing description is intended primarily for illustrative purposes. It will be readily apparent to those skilled in the art that numerous variations and modifications of the elements of structure and function described above may be modified without departing from the spirit and scope of the invention.

What is claimed is:

1. An ocular infusion cannula comprising:
   a first tube segment having an open end cut at an acute angle with respect to the axis thereof;
   a second tube segment of lesser outer diameter than said first tube segment, joined coaxially to said first tube segment at the end opposite said open end to form a shoulder; and
   a flange encircling said second tube segment and spaced apart from said shoulder.

2. An ocular infusion cannula comprising:
   a first tube segment;
   a second tube segment of lesser outer diameter than said first tube segment, joined coaxially to said first tube segment to form a shoulder;
   a flange encircling said second tube segment and spaced apart from said shoulder, and
   a third tube segment extending from said flange on the side opposite said shoulder coaxially with said first and second tube segments, said third tube segment sized for fluid-tight fit inside flexible fluid delivery tubing.

3. An ocular infusion cannula in accordance with claim 2 in which the bore in said third tube segment is of greater diameter than the bore in said second tube segment and the bore in said third tube segment contains a section tapering to the bore in said second tube segment.

4. A method for maintaining fluid pressure in an eyeball, comprising:
   (a) piercing the sclera of said eyeball with a cannula having a forward poriton and a neck portion of lesser external diameter than said forward portion thereby defining a shoulder at the juncture of said forward and neck portions, said neck portion terminating in a flange;
   (b) advancing said cannula into said eyeball until said shoulder and said flange are on opposite sides of said sclera; and
   (c) applying fluid pressure to the interior of said eyeball through said cannula.

5. A method in accordance with claim 4 further comprising attaching fluid delivery tubing to the protruding end of said cannula.

6. A method in accordance with claim 4 in which said cannula further includes a rearward portion extending rearward from said flange and of greater diameter than said neck portion, said rearward portion adapted for the attachment of fluid delivery tubing thereto, and step (c) comprises attaching fluid delivery tubing to said rearward portion.

* * * * *